United States Patent
Wang et al.

(10) Patent No.: US 11,129,863 B2
(45) Date of Patent: Sep. 28, 2021

(54) COMPOSITION, PREPARATION METHOD THEREOF, AND APPLICATION THEREOF IN THE PREVENTION AND TREATMENT OF MAMMARY GLAND DISEASE

(71) Applicant: INFINITUS (CHINA) COMPANY LTD., Guangdong (CN)

(72) Inventors: Yu Wang, Guangdong (CN); Chujie Li, Guangdong (CN); Yiting Yang, Guangdong (CN)

(73) Assignee: INFINITUS (CHINA) COMPANY LTD., Guangdong (CN)

( * ) Notice: Subject to any disclaimer, the term of this patent is extended or adjusted under 35 U.S.C. 154(b) by 5 days.

(21) Appl. No.: 16/584,815

(22) Filed: Sep. 26, 2019

(65) Prior Publication Data

US 2020/0101128 A1 Apr. 2, 2020

(30) Foreign Application Priority Data

Sep. 30, 2018 (CN) .......................... 201811155177.3

(51) Int. Cl.
*A61K 36/804* (2006.01)
*A23L 33/105* (2016.01)
*A61P 35/00* (2006.01)
*A61K 36/344* (2006.01)
*A61K 36/65* (2006.01)
*A61K 36/815* (2006.01)
*A61K 36/87* (2006.01)
*A61K 36/88* (2006.01)
*A61K 36/8905* (2006.01)

(52) U.S. Cl.
CPC .......... *A61K 36/804* (2013.01); *A23L 33/105* (2016.08); *A61K 36/344* (2013.01); *A61K 36/65* (2013.01); *A61K 36/815* (2013.01); *A61K 36/87* (2013.01); *A61K 36/88* (2013.01); *A61K 36/8905* (2013.01); *A61P 35/00* (2018.01); *A23V 2002/00* (2013.01); *A61K 2236/331* (2013.01); *A61K 2236/333* (2013.01); *A61K 2236/39* (2013.01); *A61K 2236/51* (2013.01); *A61K 2236/53* (2013.01); *A61K 2236/55* (2013.01)

(58) Field of Classification Search
None
See application file for complete search history.

(56) References Cited

PUBLICATIONS

Qian, 2010, Dr. Chen Ying-yi's Experience in Treating Premature Ovarian Failure, Journal of Traditional Chinese Medicine, 30: 217-221.*

* cited by examiner

*Primary Examiner* — Terry A Mckelvey
*Assistant Examiner* — Catheryne Chen
(74) *Attorney, Agent, or Firm* — Yue (Robert) Xu; Apex Attorneys at Law, LLP

(57) ABSTRACT

The present disclosure relates to the technical field of traditional Chinese medicine technology, especially to a composition, a preparation method thereof and an application in the prevention and treatment of mammary gland diseases. The present disclosure provides a composition consisting of Rehmanniae Radix Praeparata, Lycii Fructus, Polygonati Rhizoma, Radix Codonopsis Pilosulae, Paeoniae Radix Alba, Cyperi Rhizoma (processed with vinegar) and Grape Seed. The composition has functions of improving hyperplasia of mammary gland and/or anti-oxidation. Compared with each control group, the composition provided by the present disclosure has the optimal effects, and the effect has statistical differences, indicating that the components in the composition provided by the present disclosure are reasonably arranged and can play a good synergistic effect. Furthermore, the preparation is safe and has no side effects.

6 Claims, 5 Drawing Sheets

8-a
8-b
8-c 8-d
8-e
8-f 8-g
8-h
8-i 8-j

COMPOSITION, PREPARATION METHOD THEREOF, AND APPLICATION THEREOF IN THE PREVENTION AND TREATMENT OF MAMMARY GLAND DISEASE

CROSS REFERENCE TO RELATED APPLICATIONS

This application claims the priority of Chinese Patent Application No. 201811155177.3, filed on Sep. 30, 2018, and titled with "COMPOSITION, PREPARATION METHOD THEREOF, AND APPLICATION THEREOF IN THE PREVENTION AND TREATMENT OF MAMMARY GLAND DISEASE", and the disclosures of which are hereby incorporated by reference.

FIELD

The present disclosure relates to the field of traditional Chinese medicine technology, especially to a composition, a preparation method thereof and application thereof in the prevention and treatment of mammary gland disease.

BACKGROUND

Hyperplasia of mammary gland is the most common breast disease in women. In women of adolescence or youth, there is breast pain before menstruation, sometimes the pain spreads to the shoulders and back. After the menstruation, the breast pain gradually relieves, and only hyperplasia of mammary glands can be touched, without obvious nodules. These are physiological hyperplasia. Hyperplasia of mammary gland is a benign hyperplasia of the mammary gland mesenchyme, which is a physiological hyperplasia and subinvolution of the normal lobular of mammary gland, and is disorder of normal structure of the mammary gland, belonging to pathological hyperplasia. It is a kind of disease that is neither inflammation nor tumor. Pathological hyperplasia of the mammary gland is characterized by different degrees of hyperplasia of the lobular acinus, distal ducts and connective tissue (comprising lobular hyperplasia type, fibroadenosis type, fibrosis type), as well as highly expansion of the terminal duct-lobular unit and acinus into a cyst (cystic hyperplasia of breast). A very small part of the hyperplasia of lobular mammary gland is accompanied by ductal epithelial hyperplasia, and shows severe dysplasi, which becomes a precancerous lesion, and needs active treatment and regular check to prevent it from happening.

In western medicine, it is believed that under the action of endocrine hormones, especially estrogen/progestational hormone, with the changes of menstrual cycle, mammary gland may have changes of hyperplasia and involution. Due to the unavoidable external factors such as anxiety, stress, inactivity etc., the imbalance of endocrine hormone metabolism, increase of estrogen levels, and thus excessive hyperplasia and subinvolution of mammary gland tissue may be caused. After a period of time, the hyperplastic mammary gland tissues cannot completely disappear, thereby forming the hyperplasia of mammary gland.

At present, the treatment therapies for hyperplasia of mammary gland include: psychotherapy, traditional Chinese medicine treatment, western medicine treatment and surgical treatment. Among them, drug treatment programs are the most. However, western medicine treatment is mainly based on hormonal drugs, long-term oral administration of which will lead to a variety of adverse reactions and side effects and cause harm to the body. The traditional Chinese medicines mainly include Rukuaixiao, Rupixiao, asparagine tablets, CANELIM tablets, and Sanjieling. However, the current traditional Chinese medicines have limited therapeutic effects, including large number of medicinal materials, among which a large number are animal medicines. For example, some compositions contain animal medicines such as centipede, silkworms, which are not suitable for long-term taking. Therefore, it is of practical significance to develop an oral health care product that is safe, has no side effects, convenient for long-term use, gives consideration into both the incidental and fundamental effect, and effectively relieves breast symptoms.

SUMMARY

In view of this, the technical problem to be solved in the present disclosure is to provide a composition, a preparation method thereof and application thereof in the prevention and treatment of mammary gland disease. The composition provided here can effectively treat hyperplasia of mammary glands.

The composition in the present disclosure is consisted of the following components in parts by weight

| | |
|---|---|
| Rehmanniae Radix Praeparata | 10 parts-200 parts; |
| Lycii Fructus | 8 parts-100 parts; |
| Polygonati Rhizoma | 8 parts-100 parts; |
| Radix Codonopsis Pilosulae | 4 parts-50 parts; |
| Paeoniae Radix Alba | 4 parts-50 parts; |
| Cyperi Rhizoma (processed with vinegar) | 4 parts-50 parts; |
| Grape Seed | 1 part-30 parts. |

In some embodiments of the present disclosure, the composition is consisted of the following components in parts by weight

| | |
|---|---|
| Rehmanniae Radix Praeparata | 30 parts-150 parts; |
| Lycii Fructus | 40 parts-80 parts; |
| Polygonati Rhizoma | 40 parts-80 parts; |
| Radix Codonopsis Pilosulae | 10 parts-50 parts; |
| Paeoniae Radix Alba | 10 parts-50 parts; |
| Cyperi Rhizoma (processed with vinegar) | 10 parts-50 parts; |
| Grape Seed | 1 part-20 parts. |

In some specific embodiments, the composition is consisted of the following components in parts by weight

| | |
|---|---|
| Rehmanniae Radix Praeparata | 90 parts; |
| Lycii Fructus | 60 parts; |
| Polygonati Rhizoma | 60 parts; |
| Radix Codonopsis Pilosulae | 30 parts; |
| Paeoniae Radix Alba | 30 parts; |
| Cyperi Rhizoma (processed with vinegar) | 30 parts; |
| Grape Seed | 7 parts. |

In some specific embodiments, the composition is consisted of the following components in parts by weight

| | |
|---|---|
| Rehmanniae Radix Praeparata | 10 parts; |
| Lycii Fructus | 100 parts; |
| Polygonati Rhizoma | 8 parts; |
| Radix Codonopsis Pilosulae | 50 parts; |
| Paeoniae Radix Alba | 4 parts; |
| Cyperi Rhizoma (processed with vinegar) | 50 parts; |
| Grape Seed | 1 part. |

In some specific embodiments, the composition is consisted of the following components in parts by weight

| | |
|---|---|
| Rehmanniae Radix Praeparata | 200 parts; |
| Lycii Fructus | 8 parts; |
| Polygonati Rhizoma | 100 parts; |
| Radix Codonopsis Pilosulae | 4 parts; |
| Paeoniae Radix Alba | 50 parts; |
| Cyperi Rhizoma (processed with vinegar) | 4 parts; |
| Grape Seed | 30 parts. |

In some specific embodiments, the composition is consisted of the following components in parts by weight

| | |
|---|---|
| Rehmanniae Radix Praeparata | 30 parts; |
| Lycii Fructus | 80 parts; |
| Polygonati Rhizoma | 40 parts; |
| Radix Codonopsis Pilosulae | 50 parts; |
| Paeoniae Radix Alba | 10 parts; |
| Cyperi Rhizoma (processed with vinegar) | 50 parts; |
| Grape Seed | 1 part. |

In some specific embodiments, the composition is consisted of the following components in parts by weight

| | |
|---|---|
| Rehmanniae Radix Praeparata | 150 parts; |
| Lycii Fructus | 40 parts; |
| Polygonati Rhizoma | 80 parts; |
| Radix Codonopsis Pilosulae | 10 parts; |
| Paeoniae Radix Alba | 50 parts; |
| Cyperi Rhizoma (processed with vinegar) | 10 parts; |
| Grape Seed | 20 parts. |

The present disclosure also provides an extract, which is made from the composition of the present disclosure.

The present disclosure provides a method for preparing the extract, comprising, extracting Cyperi Rhizoma (processed with vinegar) and Paeoniae Radix Alba with water, concentrating to powder by spraying drying, to give component A;

extracting a combination of Rehmanniae Radix Praeparata, Polygonati Rhizoma, Lycii Fructus and Radix Codonopsis Pilosulae by water extraction and alcohol deposit to obtain a precipitation, and drying the precipitation to powder, to give component B;

extracting Grape Seed with an alcohol, column separating, gathering effluent fraction of ethanol, and drying the effluent fraction to powder, to give a Grape Seed Extract;

and mixing component A, component B and the Grape Seed Extract to give the extract.

In the process of water extraction of the present disclosure, the weight of water is 5-20 times based on a total weight of the medicinal materials, the extraction temperature is 80-100° C., the duration is 0.5-4 h, and the extraction is carried out for 2 times.

In a specific embodiment, the weight of water is 8 times based on a total weight of the medicinal materials, the extraction temperature is 100° C., the duration is 1 h, and the extraction is carried out for 2 times.

In the present disclosure, the concentration may be a vacuum concentration, a heating concentration, a freeze concentration, or a crystallization concentration.

The alcohol precipitation of the present disclosure is carried out by using an ethanol aqueous solution having a volume fraction of 80%-95%, until the finally volume fraction of ethanol is 75% or more.

In a specific embodiment, the alcohol precipitation is carried out by using an ethanol aqueous solution having a volume fraction of 95%, until the finally volume fraction of ethanol is 75%.

In the extraction of Grape Seed, the alcohol extraction is carried out by using an ethanol aqueous solution having a volume fraction of 65%-85%, the weight of ethanol aqueous solution is 5-20 times based on a total weight of the Grape Seed, the duration is 0.5-4 h, and the extraction is carried out for 3 times.

Specifically, the method for preparing the Grape Seed Extract comprises washing the Grape Seed, and adding the 65%-85% ethanol, in which the weight of ethanol is preferably 5-20 times based on a total weight of the Grape Seed, the extraction is preferably carried out for 3 times, and the duration of each time is 0.5-4 h; filtering, concentrating the extract solution, and carrying out a column chromatography to separate the active ingredients (procyanidine), performing a gradient elution with enthanol and collecting the eluant, concentrating, spray drying, and pulverizing to give the Grape Seed Extract.

It has been identified that the main ingredients in the aqueous extract of Paeoniae Radix Alba and Cyperi Rhizoma (processed with vinegar) are paeoniflorin and volatile oils of Cyperi Rhizoma (processed with vinegar), such as, cyperone, cyperene, cyperol, isocyperol. After extracting Rehmanniae Radix Praeparata, Polygonati Rhizoma, Lycii Fructus and Radix Codonopsis Pilosulae with water and precipitating them with an alcohol, the main ingredients of the obtained extract are polysaccharides, which are able to increase the immunity of organism and prevent the breast disease from happening. In the present disclosure, the main ingredient of the Grape Seed Extract is procyanidine, which may be self-made by alcohol extraction, or purchased from the market.

Use of the composition, the extract, or the extract prepared by the method of the present disclosure in the preparation of a product for regulating endocrine levels.

In the present disclosure, the endocrine hormone is estradiol, progesterone, luteinizing hormone, follicle stimulating hormone and/or prolactin.

The endocrine regulation according to the present invention means bidirectional regulation of endocrine hormones. In the case of abnormal increase or decrease of endocrine hormones, both the excess endocrine hormones can be converted to normal, and the too low endocrine hormones can be converted to be in a normal state, and finally the endocrine hormone levels reach equilibrium.

Estradiol ($E_2$), progesterone (P), prolactin (PRL), luteinizing hormone (LH) and follicle stimulating hormone (FSH) are closely related to the development and health of mammary gland. The researches in the present disclosure show that compared with healthy rats, levels of $E_2$, P, PRL, LH and FSH of rats having hyperplasia of mammary gland significantly increase, and their breast tissues have an expression of erected, relatively firm, hyperemic, and height-increased (2-3 mm) nipple. After administration of the composition provided in the present disclosure, the levels of $E_2$, P, PRL, LH and FSH all decrease, approaching to a normal value, and the hyperemia of nipple significantly reduces.

Specifically, use of the composition, the extract, or the extract prepared by the method of the present disclosure in the preparation of a product for inhibiting the levels of $E_2$, P, PRL, LH and FSH of patients having hyperplasia of mammary gland.

Use of the composition, the extract or the extract prepared by the method of the present disclosure in the preparation of a product for regulating expression levels of estrogen receptor and/or progesterone receptor.

Use of the composition, the extract or the extract prepared by the method in the preparation of a product for improving hyperplasia of mammary gland.

In the present disclosure, improving hyperplasia of mammary gland comprises improving diffuse hyperplasia of mammary gland, improving breast pain and/or improving breast tenderness.

In the present disclosure, the diameters and heights of the second pair of nipples of the model rats having hyperplasia of mammary gland are tested. The results show that compared with the model control group, the diameters and heights of the second pair of nipples of the rats, to which the composition of the present disclosure is administered, are significantly reduced ($p<0.01$). The results of tissue section examination show that the number of lobules of mammary gland of rats in the model group significantly increases, and the number of acinus significantly increases. As for some of the mammary glands, lumen of the acinus expands, having secreta inside. As for some of the mammary glands, epithelial cells of the ducts are significantly proliferated, locally showing papillary or multi-layer hyperplasia, dilatation of lumen, which has exfoliated epithelial cells and secreta inside, accompanying with interstitial fibrous tissue hyperplasia. On the contrary, the number of lobules of mammary gland of rats administered with the composition of the present disclosure significantly reduces, the number of acinus significantly decreases, and hyperplasia of the epithelial cells of the mammary gland duct significantly reduces. In addition, the clinical research shows that samples of subjects having slight mammary gland pain and moderate mammary gland pain are suitable samples, and samples that have developed into lesion are removed. After administration of the composition provided by the present disclosure for 3 months, degree of breast pain, degree of breast tenderness, size of lump, texture of lump and distribution range of lump were significantly improved in subjects compared to the baseline period ($p<0.05$). Especially, the improvement of degree of breast pain (51.6%) and degree of breast tenderness (51.6%) are the most significant. Compared with each control group, the composition provided in the present disclosure has optimal effects, and the effect has statistical differences, indicating that components in the composition provided in the present disclosure are reasonably arranged and can play a good synergistic effect.

Use of the composition, the extract or the extract prepared by the method in the preparation of an anti-oxidative product.

In the present disclosure, the anti-oxidation comprises lowering LPO and/or MDA levels in serum, improving total anti-oxidative capacity, improving GSH-PX enzyme activity, and improving SOD enzyme activity.

In the present disclosure, D-galactose is used to establish the oxidative damage model of rats. Compared with the normal control group, T-AOC of rats in the model control group significantly decreases ($p<0.01$), and GSH-PX activity significantly decreases ($p<0.01$). Compared with the model control group, the T-AOC of rats administered with the composition of the present disclosure significantly increases ($p<0.05$), and the GSH-PX activity significantly increases ($p<0.01$). Compared with the normal control group, the SOD activity of rats in the model control group significantly decreases ($p<0.05$), and contents of LPO and MDA significantly increase ($p<0.01$). Compared with the model control group, the SOD activity of rats administered with the composition of the present disclosure significantly increases ($p<0.01$), and the contents of LPO and MDA significantly decrease ($p<0.01$). Compared with each control group, the composition provided in the present disclosure has optimal effects, and the effect has statistical differences, indicating that components in the composition provided in the present disclosure are reasonably arranged and can play a good synergistic effect.

The present disclosure also provides a product for improving hyperplasia of mammary gland and/or anti-oxidation, comprising the composition, the extract, or the extract prepared by the method in the present disclosure.

The product for improving hyperplasia of mammary gland and/or anti-oxidation according to the present disclosure is a medicine, a health care product or a food.

Specifically, the present disclosure provides a medicine for treating hyperplasia of mammary gland. An anti-oxidant health care product or food is also provided.

The products provided in the present disclosure also include excipients.

The excipients are pharmaceutical excipient, an acceptable ingredient in food and/or an acceptable excipient in a health care product.

In the present disclosure, the dosage form of the product is an injection or an oral preparation.

The oral preparation is a powder, a tablet, a granule, a capsule, a solution, an emulsion, a suspension, a pill or a syrup.

The present disclosure further provides a method for improving hyperplasia of mammary gland, comprising administering the product provided in the present disclosure.

The method for administering is by oral administration at a dose of 2.1 g/d.

The present disclosure provides a composition consisting of Rehmanniae Radix Praeparata, Lycii Fructus, Polygonati Rhizoma, Radix Codonopsis Pilosulae, Paeoniae Radix Alba, Cyperi Rhizoma (processed with vinegar) and Grape Seed. The composition has functions of improving hyperplasia of mammary gland and/or anti-oxidation. Compared with each control group, the composition provided by the present disclosure has the optimal effects, and the effect has statistical differences, indicating that the components in the composition provided by the present disclosure are reasonably arranged and can play a good synergistic effect. After administration of the composition provided by the present disclosure, degree of breast pain, degree of breast tenderness, size of lump, texture of lump and distribution range of lump were significantly improved in subjects compared to the baseline period. Furthermore, the preparation is safe and has no side effects.

BRIEF DESCRIPTION OF DRAWINGS

FIG. 8-b shows optical microscope observation of the mammary gland tissue of model control group, 100×; FIG. 8-c shows optical microscope observation of the mammary gland tissue of composition 1 group, 100×; FIG. 8-d shows optical microscope observation of the mammary gland tissue of composition 2 group, 100×; FIG. 8-e shows optical microscope observation of the mammary gland tissue of composition 3 group, 100×; FIG. 8-f shows optical microscope observation of the mammary gland tissue of composition 4 group, 100×; FIG. 8-g shows optical microscope observation of the mammary gland tissue of composition 5 group, 100×; FIG. 8-h shows optical microscope observation of the mammary gland tissue of control sample 1 group, 100×; FIG. 8-i shows optical microscope observation of the mammary gland tissue of control sample 2 group, 100×; FIG. 8-j shows optical microscope observation of the mammary gland tissue of Rupixiao group, 100×.

DETAILED DESCRIPTION

Figure 1:
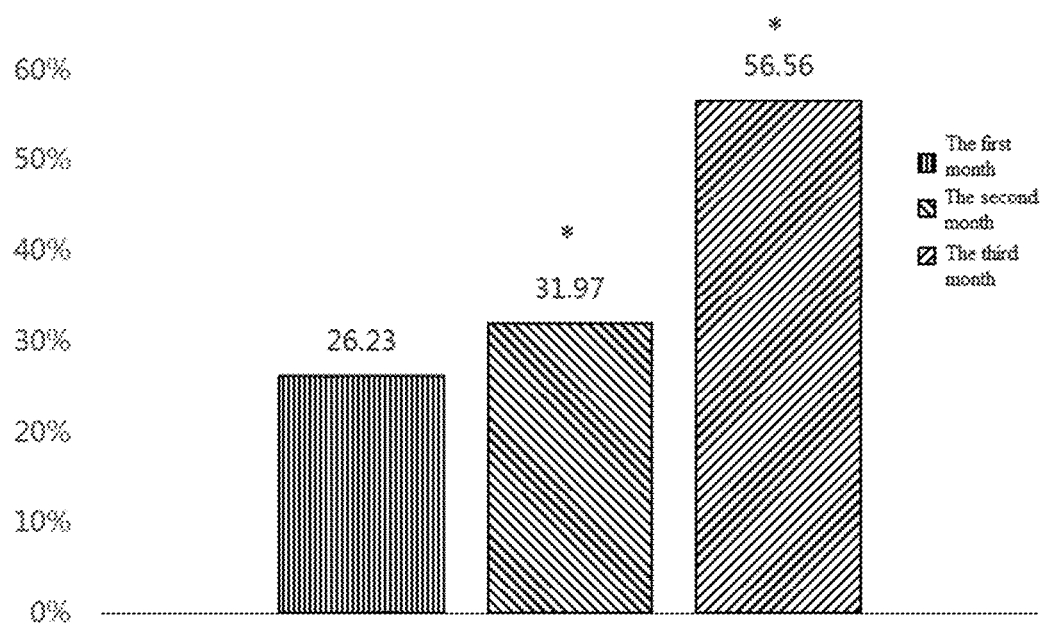
FIG. 1 shows a total evaluation of breast pain (T2B) after administering with the compositions; "*" represents the baseline of the group, and compared with the first, the second and the third month, the difference is significant ($p<0.05$); obvious improvement (TOP 2)=very obvious improvement (5-6 points)+obvious improvement (3-4 points).

The present disclosure provides a composition, a preparation method thereof and an application in the prevention and treatment of mammary gland diseases. Those skilled in the art can learn from the contents of this document and appropriately improve the process parameters. It is to be understood that all such alternatives and modifications are obvious to those skilled in the art, and are considered to be included in the present disclosure. The methods and applications of the present disclosure have been described in the preferred embodiments. It will be apparent to those skilled in the art that the methods and applications herein may be modified or changed and combined to implement and apply the techniques of the present invention without departing from the content, spirit and scope of the disclosure.

In an embodiment of the present disclosure, provided is a composition, consisting of the following components in parts by weight

| | |
|---|---|
| Rehmanniae Radix Praeparata | 10 parts-200 parts; |
| Lycii Fructus | 8 parts-100 parts; |
| Polygonati Rhizoma | 8 parts-100 parts; |
| Radix Codonopsis Pilosulae | 4 parts-50 parts; |
| Paeoniae Radix Alba | 4 parts-50 parts; |
| Cyperi Rhizoma (processed with vinegar) | 4 parts-50 parts; |
| Grape Seed | 1 part-30 parts. |

In a preferred embodiment of the present disclosure, the composition consists of the following components in parts by weight

| | |
|---|---|
| Rehmanniae Radix Praeparata | 30 parts-150 parts; |
| Lycii Fructus | 40 parts-80 parts; |
| Polygonati Rhizoma | 40 parts-80 parts; |
| Radix Codonopsis Pilosulae | 10 parts-50 parts; |
| Paeoniae Radix Alba | 10 parts-50 parts; |
| Cyperi Rhizoma (processed with vinegar) | 10 parts-50 parts; |
| Grape Seed | 1 part-20 parts. |

In a more preferred embodiment of the present disclosure, the composition consists of the following components in parts by weight

| | |
|---|---|
| Rehmanniae Radix Praeparata | 90 parts; |
| Lycii Fructus | 60 parts; |
| Polygonati Rhizoma | 60 parts; |
| Radix Codonopsis Pilosulae | 30 parts; |
| Paeoniae Radix Alba | 30 parts; |
| Cyperi Rhizoma (processed with vinegar) | 30 parts; |
| Grape Seed | 7 parts. |

In an embodiment of the present disclosure, an extract made from the composition is provided.

In an embodiment of the present disclosure, a method for preparing the extract is provided, comprising extracting Cyperi Rhizoma (processed with vinegar) and Paeoniae Radix Alba with water, concentrating to powder by spraying drying, to give component A;

extracting a combination of Rehmanniae Radix Praeparata, Polygonati Rhizoma, Lycii Fructus and Radix Codonopsis Pilosulae by water extraction and alcohol deposit to obtain a precipitation, and drying the precipitation to powder, to give component B;

extracting Grape Seed with an alcohol, column separating, gathering effluent fraction of ethanol, and drying the effluent fraction to powder, to give a Grape Seed Extract;

and mixing component A, component B and the Grape Seed Extract to give the extract.

In a preferred embodiment of the present disclosure, in the process of water extraction, the weight of water is 5-20 times based on a total weight of the medicinal materials, the extraction temperature is 80-100° C., the duration is 0.5-4 h, and the extraction is carried out for 2 times.

In a preferred embodiment of the present disclosure, the alcohol precipitation is carried out by using an ethanol aqueous solution having a volume fraction of 80%-95%, until the finally volume fraction of ethanol is 75% or more.

In an embodiment of the present disclosure, a method for regulating endocrine levels in a subject in need thereof is provided, comprising administering to the subject a therapeutically effective amount of the composition of the present disclosure.

In a preferred embodiment of the present disclosure, endocrine hormone is estradiol, progesterone, luteinizing hormone, follicle stimulating hormone and/or prolactin.

In an embodiment of the present disclosure, a method for regulating expression levels of estrogen receptor and/or progesterone receptor in a subject in need thereof is provided, comprising administering to the subject a therapeutically effective amount of the composition of the present disclosure.

In an embodiment of the present disclosure, a method for improving hyperplasia of mammary gland in a subject in need thereof is provided, comprising administering to the subject a therapeutically effective amount of the composition of the present disclosure.

In a preferred embodiment of the present disclosure, improving hyperplasia of mammary gland comprises improving diffuse hyperplasia of mammary gland, improving breast pain and/or improving breast tenderness.

In an embodiment of the present disclosure, a method for resisting oxidation is provided, comprising using the composition of the present disclosure.

In a preferred embodiment of the present disclosure, the resisting oxidation comprises lowering LPO and/or MDA levels in serum, improving total anti-oxidative capacity, improving GSH-PX enzyme activity, and improving SOD enzyme activity.

In an embodiment of the present disclosure, a product for improving hyperplasia of mammary gland and/or resisting oxidation is provided, comprising the composition of the present disclosure.

The materials used in the present disclosure are all normal products, all of which are commercially available.

The present disclosure will be further illustrated hereinafter in conjunction with the embodiments.

EXAMPLE

Formulation of the composition in each group is shown in Table 1.

TABLE 1

Formulations of the compositions (parts by weight)

| | Rehmanniae Radix Praeparata | Lycii Fructus | Polygonati Rhizoma | Radix Codonopsis Pilosulae | Paeoniae Radix Alba | Cyperi Rhizoma (processed with vinegar) | Grape Seed |
|---|---|---|---|---|---|---|---|
| Composition 1 | 90 | 60 | 60 | 30 | 30 | 30 | 7 |
| Composition 2 | 10 | 100 | 8 | 50 | 4 | 50 | 1 |
| Composition 3 | 200 | 8 | 100 | 4 | 50 | 4 | 30 |
| Composition 4 | 30 | 80 | 40 | 50 | 10 | 50 | 1 |
| Composition 5 | 150 | 40 | 80 | 10 | 50 | 10 | 20 |
| Control Example 1 | 90 | 60 | 60 | 30 | — | — | — |
| Control Example 2 | 90 | 60 | 60 | 30 | 30 | 30 | — |
| Control Example 3 | — | — | — | — | 30 | 30 | 7 |

Preparation Process

The Cyperi Rhizoma (processed with vinegar) and Paeoniae Radix Alba were mixed, drinking water was added in 8 times of the amount of the total material input, and the mixture was extracted at a heating temperature of 100° C. for 2.0 h. In a second extraction, drinking water was added in 7 times of the amount of the total material input, and the mixture was extracted at a heating temperature of 100° C. for 1.0 h. Filtration was conducted. The two extract solutions were combined and concentrated at a temperature of 65 to 85° C. and a vacuum degree of −0.04 to −0.07 Mpa, until the Solid Content was concentrated to 20±5%, following which the material was removed in hot to use. The Rehmanniae Radix Praeparata, Polygonati Rhizoma, Lycii Fructus and Radix Codonopsis Pilosulae were mixed, drinking water was added in 10 times of the amount of the total material input, and the mixture was extracted at a heating temperature of 100° C. for 2.0 h. In a second extraction, drinking water was added in 8 times of the amount of the total material input, and the mixture was extracted at a heating temperature of 100° C. for 1.0 h. Filtration was conducted. The two extract solutions were combined and concentrated at a temperature of 65 to 85° C. and a vacuum degree of −0.04 to −0.07 Mpa, until the Solid Content was concentrated to 20±5%, following which the material was removed in hot to use. Ethanol of over 85% was added, wherein the concentrated solution was added firstly and then ethanol was slowly added with stirring, until the concentration of ethanol was 75%. The resultant was stood overnight (over 12 h).

Efficacy Study

1. Inhibitory Effects on Hyperplasia of Mammary Gland 1.1 Institution that Carried Out the Experiment Guangdong Provincial Hospital of Traditional Chinese Medicine, Engineering Technology Research Institute 1.2 Object of the Experiment Inhibiting effects of the traditional Chinese medicine composition on hyperplasia of mammary gland in rats were observed and evaluated.

1.3 Experimental Materials 1.3.1 Medicinal Materials

The traditional Chinese medicine composition is provided by Infinitus (China) Co., Ltd. The blank control sample is distilled water. Positive control sample is Rupixiao tablet, Liaoning Herbapex Pharmaceutical Group Co Ltd. Estradiol benzoate injection.

1.3.2 Reagents

Estradiol benzoate injection, Shanghai General Pharmaceutical Co., Ltd., Batch No:1207241.

Progesterone injection, Shanghai General Pharmaceutical Co., Ltd., Batch No:13003146.

Enzyme Immunoassay Kit for Rat Estradiol (ELISA kit for Rat $E_2$), Shanghai Westang Biological Technology Co., Ltd., Batch No:1307251.

Enzyme Immunoassay Kit for Rat Prolactin (ELISA Kit for Rat PRL), Shanghai Westang Biological Technology Co., Ltd., Batch No:1308083.

Enzyme Immunoassay Kit for Rat Progesterone (ELISA Kit for Rat P), Shanghai Westang Biological Technology Co., Ltd., Batch No:1307251.

Enzyme Immunoassay Kit for Rat Follicle Stimulating Hormone (ELISA Kit for Rat FSH), Shanghai Westang Biological Technology Co., Ltd., Batch No:1306251.

Enzyme Immunoassay Kit for Rat Luteinizing Hormone (ELISA Kit for Rat LH), Shanghai Westang Biological Technology Co., Ltd., Batch No:1306252.

0.9% sodium chloride injection, Sichuan Kelun Pharmaceutical Co., Ltd., Batch No: M12071027.

1.3.3 Dosage Definition

Blank control group, traditional Chinese medicine formulation group 1 (752.32 mg·kg$^{-1}$), traditional Chinese medicine formulation group 2 (752.32 mg·kg$^{-1}$), traditional Chinese medicine formulation group 3 (752.32 mg·kg$^{-1}$), traditional Chinese medicine formulation group 4 (752.32 mg·kg$^{-1}$), traditional Chinese medicine formulation group 5 (752.32 mg·kg$^{-1}$), control group 1 (752.32 mg·kg$^{-1}$), control group 2 (752.32 mg·kg$^{-1}$).

1.4 Experimental Method and Test Indicators

Figure 8:
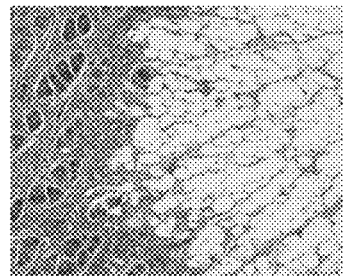
FIG. 8 shows optical microscope observation of the mammary gland tissue of each group, 100×; wherein, FIG. 8-a shows optical microscope observation of the mammary gland tissue of normal control group, 100×.
Figure 8:
Figure 8:
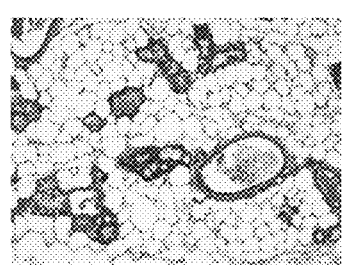
Figure 8:
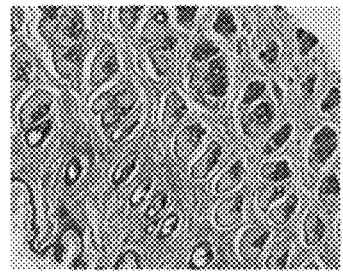
Figure 8:
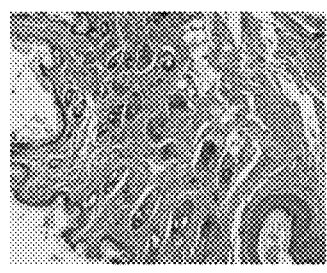
Figure 8:
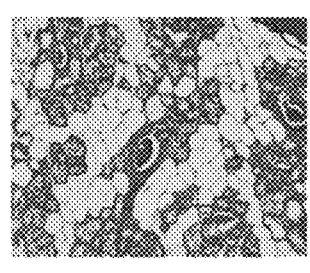
Figure 8:
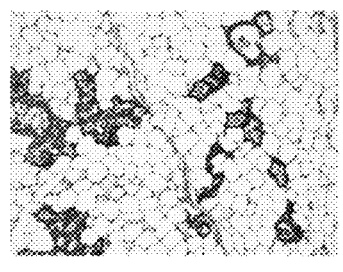
Figure 8:
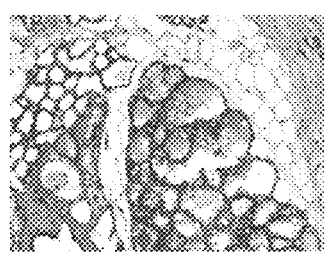
Figure 8:
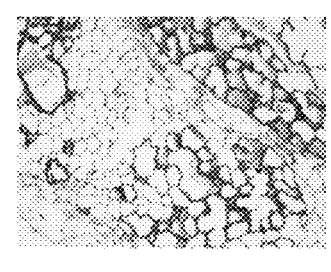
Figure 8:
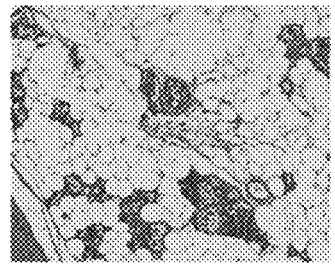

Modeling method: except for the normal control group, rats in the other groups were intramuscularly injected with 0.5 mg·kg$^{-1}$ of estradiol benzoate once a day for 25 d. Subsequently, the rats were intramuscularly injected with 4 mg·kg$^{-1}$ of progesterone once a day for 5 d. The rats in the normal control group were not injected with the hormone, but only intramuscularly injected with 0.2 ml normal saline per rat once a day for 30 d. Each administered group was intragastrically administered according to the dosage, and the normal control group and the model control group were intragastrically administered with an equal volume of distilled water. There were 10 rats in each group, administered once a day for 30 d. 1 h after the last administration, the diameters and heights of the second pair of nipples were measured with a vernier caliper, and the appearance was observed. Blood was collected from the venous plexus of orbit of the animals, and serum was separated. Contents of estradiol $E_2$, progesterone P, Prolactin PRL, luteinizing hormone LH, follicle-stimulating hormone FSH in the serum of the animals were determined. Partial depilation treatment was carried out using 8% sodium sulfide. After the animals were sacrificed, the second pair of nipples in chests of the rats was integrally peeled and taken off. The nipples were fixed with 10% formaldehyde solution, subjected to paraffin embedded section, and the second pair of mammary tissue was dyed with hematoxylin-eosin (HE) and observed with light microscope (FIG. 8).

1.5 Calculation of Q Value of Drug Combination (Jin Zhengjun Method)

Q value of drug combination was calculated using a modified formula: $Q = E_{A+B}/(E_A + E_B - E_A \times E_B)$ according to the method of literature. $E_{A+B}$ indicates the data of drug combination, $E_A$ indicates the data of a single use of A, $E_B$ indicates the data of a single use of B, and the calculation is performed using the inhibition rate or the increase rate data. A Q value of less than 0.85 indicates that the two drugs have an antagonistic effect after combination; a Q value of greater than 0.85 and less than 1.15 indicates that the two drugs have an additive effect after combination; a Q value of greater than 1.15 indicates that the two drugs have a synergistic effect after combination.

1.6 Experimental Results 1.6.1 Influence on Diameters and Heights of the Second Pair of Nipples of the Rats Having Hyperplasia of Mammary Gland 1 h after the last administration, the diameters and heights of the second pair of nipples were measured with a vernier caliper, and the appearance was observed.

TABLE 2

Influence on the diameters and heights of the second pair of nipples of the rats having hyperplasia of mammary gland (x ± s, n = 10)

| Group | Dosage | Diameter of nipple (mm) | Inhibition rate | Height of nipple (mm) | Inhibition rate |
|---|---|---|---|---|---|
| Normal control group | / | 1.89 ± 0.09 | — | 1.61 ± 0.07 | — |
| Model control group | / | 2.60 ± 0.10** | — | 2.47 ± 0.08** | — |
| Composition 1 | 752.32 mg·kg$^{-1}$ | 2.19 ± 0.07$^{\#\#}$ | 16.00% | 1.98 ± 0.06$^{\#\#}$ | 20.10% |
| Composition 2 | 752.32 mg·kg$^{-1}$ | 2.35 ± 0.08$^{\#\#\Delta\Delta}$ | 9.50% | 2.18 ± 0.08$^{\#\#\Delta\Delta}$ | 12.10% |
| Composition 3 | 752.32 mg·kg$^{-1}$ | 2.26 ± 0.08$^{\#\#\Delta}$ | 13.10% | 2.19 ± 0.05$^{\#\#\Delta\Delta}$ | 11.50% |
| Composition 4 | 752.32 mg·kg$^{-1}$ | 2.27 ± 0.07$^{\#\#\Delta}$ | 12.70% | 2.13 ± 0.06$^{\#\#\Delta\Delta}$ | 13.70% |
| Composition 5 | 752.32 mg·kg$^{-1}$ | 2.26 ± 0.07$^{\#\#\Delta}$ | 13.10% | 2.18 ± 0.06$^{\#\#\Delta\Delta}$ | 11.80% |
| Control Sample 1 | 752.32 mg·kg$^{-1}$ | 2.47 ± 0.11$^{\Delta\Delta☆☆◊◊▽▽▷▷}$ | 5.2% | 2.35 ± 0.06$^{\Delta\Delta☆☆◊◊▽▽▷▷}$ | 5.00% |
| Control Sample 2 | 752.32 mg·kg$^{-1}$ | 2.50 ± 0.08$^{\Delta\Delta☆☆◊◊▽▽▷▷}$ | 3.8% | 2.37 ± 0.08$^{\Delta\Delta☆☆◊◊▽▽▷▷}$ | 4.4% |
| Control Sample 3 | 752.32 mg·kg$^{-1}$ | 2.46 ± 0.10$^{\Delta\Delta☆◊◊▽▽▷▷}$ | 5.5% | 2.44 ± 0.11$^{\Delta\Delta☆☆◊◊▽▽▷▷}$ | 1.5% |
| Rupixiao tablet group | 960.00 mg·kg$^{-1}$ | 2.28 ± 0.06$^{\#\#}$ | 12.50% | 2.15 ± 0.09$^{\#\#}$ | 12.90% |

Comments: Compared with the normal control group, *p < 0.05, and **p < 0.01.
Compared with the model control group, #p < 0.05, and ##p < 0.01.
Compared with composition group 1, $^{\Delta}$p < 0.05, and $^{\Delta\Delta}$p < 0.01.
Compared with composition group 2, $^{☆}$p < 0.05, and $^{☆☆}$p < 0.01.
Compared with composition group 3, $^{◊}$p < 0.05, and $^{◊◊}$p < 0.01.
Compared with composition group 4, $^{▽}$p < 0.05, and $^{▽▽}$p < 0.01.
Compared with composition group 5, $^{▷}$p < 0.05, and $^{▷▷}$p < 0.01.

Results: The degree of hyperplasia of mammary gland of human was irregular, and was usually localized mass; whereas the hyperplasia of mammary gland of rats was usually diffusive, showing an increase in the overall size of the breast, an increase in the height and the diameter of the nipples. In the results of the present experiment, compared with the normal control group, the diameters and heights of the second pair of nipples of the rats in the model control group significantly increased (p<0.01). Compared with the model control group, the diameters and heights of the second pair of nipples of the rats in the formulation groups 1, 2, 3, 4, 5 and the Rupixiao tablet group significantly decreased (p<0.01). The diameters and heights of the second pair of nipples of the rats in the formulation groups 2, 3, 4, 5 were all larger than those of the formulation group 1 (p<0.01 or p<0.05). The diameters and heights of the second pair of nipples of the rats in the control sample group 1 were all larger than those of the formulation groups 1, 2, 3, 4, 5 (p<0.01). The diameters and heights of the second pair of nipples of the rats in the control sample group 2 were all larger than those of the formulation groups 1, 2, 3, 4, 5 (p<0.01). The diameters and heights of the second pair of nipples of the rats in the control sample group 3 were all larger than those of the formulation groups 1, 2, 3, 4, 5 (p<0.01 or p<0.05). $E_{composition\ 1}$ Q value= $E_{composition\ 1}/(E_{control\ sample1}+E_{control\ sample3}-E_{control\ sample1}*E_{control\ sample3})=0.160/(0.052+0.055-0.052*0.055)=1.536$. $1.536>1.15$, indicating that the combination of control sample 1 and control sample 3 has a synergistic effect on decreasing the diameter of nipple. $E_{composition\ 1}$ Q value=$E_{composition\ 1}/(E_{control\ sample1}+E_{control\ sample3}-E_{control\ sample1}*E_{control\ sample3})=0.201/(0.050+0.015-0.050*0.015)=3.152$, $3.152>1.15$, indicating that the combination of control sample 1 and control sample 3 has a synergistic effect on decreasing the height of nipple.

1.6.2 Influence on Contents of Estradiol $E_2$ and Progesterone P in Serum of the Rats Having Hyperplasia of Mammary Gland Blood was collected from the venous plexus of orbit of the animals, and the serum was separated. Contents of estradiol $E_2$ and progesterone P in serum of the animals were determined.

TABLE 3

Influence on contents of estradiol $E_2$ and progesterone P in serum of the rats having hyperplasia of mammary gland ($\bar{x} \pm s$, n = 10)

| Group | Dosage | Estradiol $E_2$ (pg/ml) | Inhibition rate | Progesterone P (pg/ml) | Inhibition rate |
|---|---|---|---|---|---|
| Normal control group | / | 59.95 ± 13.79 | — | 64.92 ± 18.39 | — |
| Model control group | / | 491.30 ± 83.82** | — | 225.32 ± 32.96** | — |
| Composition 1 | 752.32 mg·kg$^{-1}$ | 315.76 ± 54.04$^{\#\#}$ | 35.73% | 164.17 ± 20.65$^{\#\#}$ | 27.14% |
| Composition 2 | 752.32 mg·kg$^{-1}$ | 396.81 ± 70.11$^{\#\#\Delta}$ | 19.23% | 172.87 ± 19.24$^{\#\#}$ | 23.28% |
| Composition 3 | 752.32 mg·kg$^{-1}$ | 343.76 ± 51.46$^{\#\#}$ | 30.03% | 175.39 ± 23.04$^{\#\#}$ | 22.16% |
| Composition 4 | 752.32 mg·kg$^{-1}$ | 386.65 ± 53.3$^{\#\#\Delta\Delta}$ | 21.30% | 174.14 ± 24.93$^{\#\#}$ | 22.71% |
| Composition 5 | 752.32 mg·kg$^{-1}$ | 374.15 ± 49.2$^{\#\#\Delta}$ | 23.84% | 173.04 ± 32.53$^{\#\#}$ | 23.20% |
| Control Sample 1 | 752.32 mg·kg$^{-1}$ | 448.79 ± 62.79$^{\Delta\Delta\star\diamond\diamond\triangledown_{\triangleright\triangleright}}$ | 8.65% | 201.13 ± 24.56$^{\Delta\star\diamond\diamond\triangledown_{\triangleright}}$ | 10.74% |
| Control Sample 2 | 752.32 mg·kg$^{-1}$ | 463.33 ± 51.12$^{\Delta\Delta\star\diamond\diamond\triangledown\triangledown_{\triangleright\triangleright}}$ | 5.69% | 207.64 ± 30.29$^{\Delta\Delta\star\diamond\triangledown_{\triangleright}}$ | 7.85% |
| Control Sample 3 | 752.32 mg·kg$^{-1}$ | 470.30 ± 46.22$^{\Delta\Delta\star\diamond\diamond\triangledown\triangledown_{\triangleright\triangleright}}$ | 4.27% | 205.30 ± 25.77$^{\Delta\Delta\star\star\diamond\triangledown_{\triangleright}}$ | 8.89% |
| Rupixiao tablet group | 960.00 mg·kg$^{-1}$ | 324.39 ± 74.32$^{\#\#}$ | 33.97% | 184.79 ± 27.75$^{\#\#}$ | 17.99% |

Comments: Compared with the normal control group, *p < 0.05, and **p < 0.01.
Compared with the model control group, #p < 0.05, and ##p < 0.01.
Compared with composition group 1, $^{\Delta}$p < 0.05, and $^{\Delta\Delta}$p < 0.01.
Compared with composition group 2, $^{\star}$p < 0.05, and $^{\star\star}$p < 0.01.
Compared with composition group 3, $^{\diamond}$p < 0.05, and $^{\diamond\diamond}$p < 0.01.
Compared with composition group 4, $^{\triangledown}$p < 0.05, and $^{\triangledown\triangledown}$p < 0.01.
Compared with composition group 5, $^{\triangleright}$p < 0.05, and $^{\triangleright\triangleright}$p < 0.01.

Results: Compared with the normal control group, the contents of estradiol $E_2$ and progesterone P of the rats in the model control group significantly increased (p<0.01). Compared with the model control group, the contents of estradiol $E_2$ and progesterone P of the rats in composition groups 1, 2, 3, 4, 5 significantly decreased (p<0.01). The content of $E_2$ in the composition groups 2, 4, 5 was higher than that in composition group 1 (p<0.01 or p<0.05). The contents of estradiol $E_2$ and progesterone P in control sample groups 1, 2, 3 were higher than those in composition groups 1, 2, 3, 4, 5 (p<0.01 or p<0.05). $E_{composition1}$ Q value=$E_{composition1}/(E_{control\ sample1}+E_{control\ sample3}-E_{control\ sample1}\times E_{control\ sample3})=0.357/(0.087+0.043-0.087\times0.043)=2.846$. $2.846>1.15$, indicating that the combination of control sample 1 and control sample 3 has a synergistic effect on decreasing $E_2$. $E_{composition1}$ Q value=$E_{composition1}/(E_{control\ sample1}+E_{control\ sample3}-E_{control\ sample1}\times E_{control\ sample3})=0.271/(0.107+0.088-0.107\times0.088)=1.454$. $1.454>1.15$, indicating that the combination of control sample 1 and control sample 3 has a synergistic effect on decreasing P.

1.6.3 Influence on Contents of Prolactin PRL, Luteinizing Hormone LH, Follicle Stimulating Hormone FSH in Serum of the Rats Having Hyperplasia of Mammary Gland At the end of the experiment, blood was collected from the venous plexus of orbit of the animals, and the serum was separated. Contents of prolactin PRL, luteinizing hormone LH, follicle stimulating hormone FSH in serum of the animals were determined.

TABLE 4

Influence on contents of PRL, LH, FSH in serum of the rats having hyperplasia of mammary gland ($\bar{x} \pm s$, n = 10)

| Group | Dosage | Prolactin PRL (pg/ml) | Inhibition rate | Luteinizing hormone LH (pg/ml) | Inhibition rate | Follicle stimulating hormone FSH (pg/ml) | Inhibition rate |
|---|---|---|---|---|---|---|---|
| Normal control group | / | 1.25 ± 0.12 | — | 2.48 ± 0.34 | — | 6.50 ± 1.65 | — |
| Model control group | / | 8.13 ± 1.13** | — | 3.83 ± 0.42** | — | 19.07 ± 4.40** | — |
| Composition 1 | 752.32 mg·kg$^{-1}$ | 3.92 ± 1.96## | 51.80% | 2.63 ± 0.30## | 31.20% | 13.49 ± 2.25## | 29.30% |
| Composition 2 | 752.32 mg·kg$^{-1}$ | 5.75 ± 1.67##Δ | 29.20% | 3.10 ± 0.28##ΔΔ | 19.20% | 14.57 ± 2.72## | 23.60% |
| Composition 3 | 752.32 mg·kg$^{-1}$ | 4.27 ± 1.91## | 47.50% | 2.84 ± 0.32## | 26.00% | 14.30 ± 3.47## | 25.00% |
| Composition 4 | 752.32 mg·kg$^{-1}$ | 3.88 ± 1.05## | 52.30% | 3.14 ± 0.29##ΔΔ | 18.00% | 14.67 ± 3.05## | 23.10% |
| Composition 5 | 752.32 mg·kg$^{-1}$ | 4.65 ± 1.11## | 42.80% | 3.04 ± 0.59##Δ | 20.80% | 14.45 ± 3.81## | 24.20% |
| Control Sample 1 | 752.32 mg·kg$^{-1}$ | 7.57 ± 1.86ΔΔ☆☆◊◊▽▽▷ | 6.80% | 3.69 ± 0.42Δ☆◊◊▽▷ | 3.7% | 17.82 ± 2.10Δ☆◊◊▽▷ | 6.60% |
| Control Sample 2 | 752.32 mg·kg$^{-1}$ | 7.49 ± 1.12ΔΔ☆☆◊◊▽▷ | 7.90% | 3.61 ± 0.43Δ☆◊▽▷ | 5.7% | 17.78 ± 3.06Δ◊▽▷ | 6.80% |
| Control Sample 3 | 752.32 mg·kg$^{-1}$ | 7.90 ± 1.10ΔΔ☆☆◊◊▽▽▷▷ | 2.80% | 3.63 ± 0.56ΔΔ☆☆◊◊▽▷ | 5.2% | 17.62 ± 2.23ΔΔ☆☆◊▽▷ | 7.60% |
| Rupixiao tablet group | 960.00 mg·kg$^{-1}$ | 4.36 ± 1.11## | 46.40% | 2.77 ± 0.40## | 27.60% | 14.85 ± 3.17## | 22.10% |

Comments: Compared with the normal control group, *p < 0.05, and **p < 0.01.
Compared with the model control group, #p < 0.05, and ##p < 0.01.
Compared with composition group 1, $^{\Delta}$p < 0.05, and $^{\Delta\Delta}$p < 0.01.
Compared with composition group 2, $^{☆}$p < 0.05, and$^{☆☆}$p < 0.01.
Compared with composition group 3, $^{◊}$p < 0.05, and $^{◊◊}$p < 0.01.
Compared with composition group 4, $^{▽}$p < 0.05, and $^{▽▽}$p < 0.01.
Compared with composition group 5, $^{▷}$p < 0.05, and $^{▷▷}$p < 0.01.

Results: Compared with the normal control group, the contents of prolactin PRL, luteinizing hormone LH and follicle stimulating hormone FSH of the rats in the model control group significantly increased (p<0.01). Compared with the model control group, the contents of prolactin PRL, luteinizing hormone LH and follicle stimulating hormone FSH of the rats in the composition groups 1, 2, 3, 4, 5 and the Rupixiao tablet group significantly decreased (p<0.01). The content of PRL of composition group 2 was higher than that of composition group 1 (p<0.05). The content of LH of composition groups 2, 4, 5 was higher than that of composition 1 (p<0.01 or p<0.05). The contents of prolactin PRL, luteinizing hormone LH, and follicle stimulating hormone FSH of control sample groups 1, 2, 3 were higher than those of composition groups 1, 2, 3, 4, 5 (p<0.01 or p<0.05). $E_{composition\ 1}$ Q value=$E_{composition\ 1}/(E_{control\ sample\ 1}+E_{control\ sample\ 3}-E_{control\ sample\ 1}\times E_{control\ sample\ 3})$=0.518/(0.068+0.028−0.068×0.028)=5.460, 5.460>1.15, indicating that the combination of control sample 1 and control sample 3 has a synergistic effect on decreasing PRL. $E_{composition\ 1}$ Q value=$E_{composition\ 1}/(E_{control\ sample\ 1}+E_{control\ sample\ 3}-E_{control\ sample\ 1}\times E_{control\ sample\ 3})$=0.312/(0.037+0.052−0.037×0.052)=3.595, 3.595>1.15, indicating that the combination of control sample 1 and control sample 3 has a synergistic effect on decreasing LH. $E_{composition\ 1}$ Q value=$E_{composition\ 1}/(E_{control\ sample\ 1}+E_{control\ sample\ 3}-E_{control\ sample\ 1}\times E_{control\ sample\ 3})$=0.293/(0.066+0.076−0.066×0.076)=2.139, 2.139>1.15, indicating that the combination of control sample 1 and control sample 3 has a synergistic effect on decreasing FSH.

1.6.4 Pathology Morphologic Observation of the Second Pair of Nipples of the Rats Having Hyperplasia of Mammary Gland At the end of the experiment, the second pair of nipples in chests of the rats was taken off. The nipples were fixed with 10% formaldehyde solution, subjected to paraffin embedded section, and the second pair of mammary tissue was dyed with hematoxylin-eosin (HE) and observed with light microscope. The results were shown in FIG. 8.

Results: In a general observation, the morphology of nipples in the normal control group was the same as that at the beginning of the experiment. The position of the nipples was not visible through the hair. After the hair was separated, the nipples were millet-like, which were clung to the skin, pale, soft, and a few nipples were slightly swelled (about 1 mm). The morphological changes of the rats in the model group having hyperplasia of mammary gland were characterized by erected, firmer, hyperemic, and height-increased nipples (2-3 mm). The nipple morphology of rats in the Chinese medicine formulation group in each dose showed that the nipples were erected, and the hyperemia significantly decreased. When observing under a microscope, there was no obvious hyperplasia in lobules of mammary gland and acinus in the normal control group. The number of acinus was 4-5, and the lumen of acinar did not expand. The number of lobules of mammary gland of rats in the model group significantly increased, and the number of acinus significantly increased. As for some of the mammary glands, lumen of the acinus expanded, having secreta inside. As for some of the mammary glands, epithelial cells of the ducts were significantly proliferated, locally showing papillary or multi-layer hyperplasia, dilatation of lumen, which had exfoliated epithelial cells and secreta inside, accompanying with interstitial fibrous tissue hyperplasia. The number of lobules of mammary gland of rats in the Chinese medicine formulation group in each dose significantly reduced, the number of acinus significantly decreased, and hyperplasia of the epithelial cells of the mammary gland duct significantly reduced. The number of lobules of mammary gland in control sample groups 1, 2 and 3 significantly increased, the number of acinus significantly increased, and hyperplasia of the epithelial cells of the mammary gland duct significantly increased.

1.7 Experimental Results

In the present disclosure, the present formulation in each dose and the Rupixiao tablet had significantly inhibitory effects on hyperplasia of mammary gland of the rats, and the drug combination in high dose group had the best overall effect.

2. Research on Anti-Oxidation Effect 2.1 Object of the Experiment

Anti-oxidation effects of the traditional Chinese medicine composition were observed and evaluated.

2.2 Experimental Materials 2.2.1 Medicinal Materials

The traditional Chinese medicine composition is provided by Infinitus (China) Co., Ltd. The blank control sample is distilled water. Positive control sample is Pingxiao capsule, national medicine permission number Z61021330, Xi'an C.P. Pharmaceutical Co. Ltd.

2.2.2 Reagents

D-(+)-Galactose, Sinopharm Chemical Reagent Co., Ltd., Batch No: 20130917.

Total Antioxidant Capacity (T-AOC) kit, Nanjing Jiancheng Bioengineering Institute, Batch No.: 20131211.

Glutathione-peroxidase (GSH-PX) kit, Nanjing Jiancheng Bioengineering Institute, Batch No.: 20140220.

Superoxide dismutase (SOD) kit measured by WST-1 method, Nanjing Jiancheng Bioengineering Institute, Batch No.: 20140416.

Lipid Peroxide (LPO) kit, Nanjing Jiancheng Bioengineering Institute, Batch No.: 20140228.

Malondialdehyde (MDA) kit, Nanjing Jiancheng Bioengineering Institute, Batch No.: 20140225.

2.2.3 Dosage Definition

Blank control group, traditional Chinese medicine formulation group 1 (752.32 mg·kg$^{-1}$), traditional Chinese medicine formulation group 2 (752.32 mg·kg$^{-1}$), traditional Chinese medicine formulation group 3 (752.32 mg·kg$^{-1}$), traditional Chinese medicine formulation group 4 (752.32 mg·kg$^{-1}$), traditional Chinese medicine formulation group 5 (752.32 mg·kg$^{-1}$), control group 1 (752.32 mg·kg$^{-1}$), control group 2 (752.32 mg·kg$^{-1}$).

2.3 Experimental Method and Test Indicators

80 SPF grade female SD rats were taken, which were randomly divided into 10 rats as the normal control group, and the other 70 rats as the model group. The rats in model groups were injected intraperitoneally with 125 mg/kgBW of D-galactose at an injection amount of 0.2 mL/100 g once a day for 6 weeks. The 10 rats in the normal control group were injected intraperitoneally with the same volume of normal saline. 6 weeks after modeling, blood was collected to measure the MDA. The rats were grouped according to the levels of MDA, which were respectively model control group, Chinese medicine formulation group, control sample group and Pingxiao capsule group, with 10 rats in each group.

Each administration group was intragastrically administered with different concentrations of test samples. The normal control group and the model control group were intragastrically injected with an equal volume of distilled water once a day for 30 d. While administering the test samples, the model control group and each administration group were continuously intraperitoneally injected with an equal amount of D-galactose. At the end of the experiment, the animals were sacrificed, and blood was collected to determine the total anti-oxidative capacity (T-AOC) of serum and contents of glutathione-peroxidase (GSH-PX), lipid peroxide (LPO), malondialdehyde (MDA) and superoxide dismutase (SOD).

2.4 Calculation of Q Value of Drug Combination (Jin Zhengjun Method)

Q value of drug combination was calculated using a modified formula: $Q=E_{A+B}/(E_A+E_B-E_A \times E_B)$ according to the method of literature. $E_{A+B}$ indicates the data of drug combination, $E_A$ indicates the data of a single use of A, $E_B$ indicates the data of a single use of B, and the calculation is performed using the inhibition rate or the increase rate data. A Q value of less than 0.85 indicates that the two drugs have an antagonistic effect after combination; a Q value of greater than 0.85 and less than 1.15 indicates that the two drugs have an additive effect after combination; a Q value of greater than 1.15 indicates that the two drugs have a synergistic effect after combination.

Experimental Results 2.5.1 Influences on T-AOC and GSH-PX of D-Galactose-Induced Aging Rats At the end of the experiment, the animals were sacrificed, and blood was collected to determine the total anti-oxidative capacity (T-AOC) and glutathione-peroxidase (GSH-PX) of serum.

TABLE 5

Influences on T-AOC and GSH-PX of D-galactose-induced aging rats ($\bar{x} \pm s$, n = 10)

| Group | Dosage | T-AOC | Increase rate | GSH-PX | Increase rate |
|---|---|---|---|---|---|
| Normal control group | / | 11.48 ± 3.88 | — | 368.87 ± 145.03 | — |

TABLE 5-continued

Influences on T-AOC and GSH-PX of D-galactose-induced aging rats ($\bar{x} \pm s$, n = 10)

| Group | Dosage | T-AOC | Increase rate | GSH-PX | Increase rate |
|---|---|---|---|---|---|
| Model control group | / | 3.39 ± 2.05** | — | 218.56 ± 38.38** | — |
| Composition 1 | 752.32 mg · kg$^{-1}$ | 8.86 ± 3.34$^{\#\#}$ | 161.30% | 320.56 ± 40.54$^{\#\#}$ | 46.70% |
| Composition 2 | 752.32 mg · kg$^{-1}$ | 6.89 ± 2.48$^{\#\#}$ | 103.30% | 302.22 ± 33.48$^{\#\#}$ | 38.30% |
| Composition 3 | 752.32 mg · kg$^{-1}$ | 7.27 ± 3.09$^{\#\#}$ | 114.60% | 322.89 ± 36.68$^{\#\#}$ | 47.70% |
| Composition 4 | 752.32 mg · kg$^{-1}$ | 8.18 ± 2.91$^{\#\#}$ | 141.40% | 314.33 ± 33.59$^{\#\#}$ | 43.80% |
| Composition 5 | 752.32 mg · kg$^{-1}$ | 7.08 ± 3.53$^{\#}$ | 108.90% | 302.19 ± 26.45$^{\#\#}$ | 38.30% |
| Control Sample 1 | 752.32 mg · kg$^{-1}$ | 4.52 ± 1.59$^{\triangle\triangle \star \diamond \triangledown\triangledown \triangleright}$ | 33.30% | 276.35 ± 24.18$^{\triangle\triangle \star \diamond \triangledown \triangleright}$ | 26.40% |
| Control Sample 2 | 752.32 mg · kg$^{-1}$ | 4.26 ± 1.48$^{\triangle\triangle \star \diamond \triangledown\triangledown \triangleright}$ | 25.80% | 260.77 ± 33.63$^{\triangle\triangle \star\star \diamond \diamond \triangledown\triangledown \triangleright}$ | 19.30% |
| Control Sample 3 | 752.32 mg · kg$^{-1}$ | 4.59 ± 1.64$^{\triangle\triangle \star \diamond \triangledown\triangledown \triangleright}$ | 35.40% | 261.30 ± 33.57$^{\triangle\triangle \star\star \diamond \diamond \triangledown\triangledown \triangleright\triangleright}$ | 19.60% |
| Pingxiao capsule group | 960.00 mg · kg$^{-1}$ | 7.50 ± 2.42$^{\#\#}$ | 121.10% | 325.09 ± 28.67$^{\#\#}$ | 48.70% |

Comments: Compared with the normal control group, *p < 0.05, and **p < 0.01.
Compared with the model control group, #p < 0.05, and ##p < 0.01.
Compared with composition group 1, $^{\triangle}$p < 0.05, and $^{\triangle\triangle}$p < 0.01.
Compared with composition group 2, $^{\star}$p < 0.05, and $^{\star\star}$p < 0.01.
Compared with composition group 3, $^{\diamond}$p < 0.05, and $^{\diamond\diamond}$p < 0.01.
Compared with composition group 4, $^{\triangledown}$p < 0.05, and $^{\triangledown\triangledown}$p < 0.01.
Compared with composition group 5, $^{\triangleright}$p < 0.05, and $^{\triangleright\triangleright}$p < 0.01.

Results: Compared with the normal control group, the T-AOC of rats in the model control group significantly decreased (p<0.01) and the GSH-PX activity significantly decreased (p<0.05). Compared with the model control group, the content of T-AOC of rats in the composition groups 1, 2, 3, 4, 5 significantly increased, and the GSH-PX activity significantly increased, showing a significant difference (p<0.01 or p<0.05). The content of T-AOC of rats in the control sample groups 1, 2 and 3 was significantly lower than that of the composition groups 1, 2, 3, 4 and 5, and the GSH-PX activity was significantly lower than that of the composition groups 1, 2, 3, 4 and 5 (p<0.01 or p<0.05). $E_{composition\ 1}$ Q value=$E_{composition\ 1}$/($E_{control\ sample\ 1}$+$E_{control\ sample\ 3}$−$E_{control\ sample\ 1}$×$E_{control\ sample\ 3}$)=1.613/(0.333+0.354−0.333×0.354)=2.006. 2.006>1.15, indicating that the combination of control sample 1 and control sample 3 has a synergistic effect on increasing T-AOC. $E_{composition\ 1}$ Q value=$E_{composition\ 1}$/($E_{control\ sample\ 1}$+$E_{control\ sample\ 3}$−$E_{control\ sample\ 1}$×$E_{control\ sample\ 3}$)=0.467/(0.264+0.196−0.264×0.196)=0.912. 0.85<0.912<1.15, indicating that the combination of control sample 1 and control sample 3 has an additive effect, working together to increase the level of GSH.

2.5.2 Influence on Contents of SOD, LPO and MDA of D-Galactose-Induced Aging Rats At the end of the experiment, blood was collected to determine the contents of lipid peroxide (LPO) and malondialdehyde (MDA), and superoxide dismutase (SOD) in serum.

TABLE 6

Influence on contents of SOD, LPO and MDA of D-galactose-induced aging rats ($\bar{x} \pm s$, n = 10)

| Group | Dosage | SOD | Increase rate | LPO | Inhibition rate | MDA | Inhibition rate |
|---|---|---|---|---|---|---|---|
| Normal control group | / | 103.10 ± 19.26 | — | 5.51 ± 0.70 | — | 2.68 ± 1.20 | — |
| Model control group | / | 75.09 ± 14.82** | — | 11.34 ± 3.69** | — | 12.83 ± 0.85** | — |
| Composition 1 | 752.32 mg · kg$^{-1}$ | 110.37 ± 14.82$^{\#\#}$ | 47.00% | 6.09 ± 1.10$^{\#\#}$ | 46.30% | 5.57 ± 1.22$^{\#\#}$ | 56.60% |
| Composition 2 | 752.32 mg · kg$^{-1}$ | 107.73 ± 20.72$^{\#\#}$ | 43.50% | 6.38 ± 1.15$^{\#\#}$ | 43.70% | 6.03 ± 0.99$^{\#\#}$ | 53.00% |
| Composition 3 | 752.32 mg · kg$^{-1}$ | 108.18 ± 21.88$^{\#\#}$ | 44.10% | 6.82 ± 0.91$^{\#\#}$ | 39.90% | 6.30 ± 1.20$^{\#\#}$ | 50.90% |
| Composition 4 | 752.32 mg · kg$^{-1}$ | 106.94 ± 23.09$^{\#\#}$ | 42.40% | 7.56 ± 1.22$^{\#\#\triangle}$ | 33.40% | 6.70 ± 0.82$^{\#\#\triangle}$ | 47.70% |

TABLE 6-continued

Influence on contents of SOD, LPO and MDA of D-galactose-induced aging rats
($\bar{x} \pm s$, n = 10)

| Group | Dosage | SOD | Increase rate | LPO | Inhibition rate | MDA | Inhibition rate |
|---|---|---|---|---|---|---|---|
| Composition 5 | 752.32 mg · kg$^{-1}$ | 109.56 ± 16.60$^{\#\#}$ | 45.90% | 7.12 ± 1.08$^{\#\#\Delta}$ | 37.20% | 7.44 ± 0.97$^{\#\#\Delta\Delta}$ | 42.00% |
| Control Sample 1 | 752.32 mg · kg$^{-1}$ | 90.50 ± 11.85$^{\Delta\Delta\star\diamond\triangledown\triangleright}$ | 20.50% | 10.27 ± 1.41$^{\Delta\Delta\star\star\diamond\diamond\triangledown\triangledown\triangleright\triangleright}$ | 9.40% | 10.00 ± 1.68$^{\Delta\Delta\star\star\diamond\diamond\triangledown\triangledown\triangleright\triangleright}$ | 22.00% |
| Control Sample 2 | 752.32 mg · kg$^{-1}$ | 90.43 ± 13.13$^{\Delta\Delta\star\diamond\triangledown\triangleright}$ | 20.40% | 9.72 ± 1.45$^{\Delta\Delta\star\star\diamond\diamond\triangledown\triangledown\triangleright\triangleright}$ | 14.30% | 10.33 ± 1.82$^{\Delta\Delta\star\star\diamond\diamond\triangledown\triangledown\triangleright\triangleright}$ | 19.50% |
| Control Sample 3 | 752.32 mg · kg$^{-1}$ | 89.90 ± 14.48$^{\Delta\Delta\star\diamond\triangledown\triangleright}$ | 19.70% | 9.86 ± 1.31$^{\Delta\Delta\star\star\diamond\diamond\triangledown\triangledown\triangleright\triangleright}$ | 13.00% | 9.84 ± 2.02$^{\Delta\Delta\star\star\diamond\diamond\triangledown\triangledown\triangleright\triangleright}$ | 23.30% |
| Pingxiao capsule group | 960.00 mg · kg$^{-1}$ | 102.48 ± 7.33$^{\#\#}$ | 36.50% | 8.76 ± 1.30$^{\#}$ | 22.70% | 8.24 ± 1.12$^{\#\#}$ | 35.70% |

Comments: Compared with the normal control group, *p < 0.05, and **p < 0.01.
Compared with the model control group, #p < 0.05, and ##p < 0.01.
Compared with the composition group 1, $^{\Delta}$p < 0.05, and $^{\Delta\Delta}$p < 0.01.
Compared with the composition group 2, $^{\star}$p < 0.05, and $^{\star\star}$p < 0.01.
Compared with the composition group 3, $^{\diamond}$p < 0.05, and $^{\diamond\diamond}$p < 0.01.
Compared with the composition group 4, $^{\triangledown}$p < 0.05, and $^{\triangledown\triangledown}$p < 0.01.
Compared with the composition group 5, $^{\triangleright}$p < 0.05, and $^{\triangleright\triangleright}$p < 0.01.

Results: Compared with the normal control group, the SOD activity of rats in the model control group significantly decreased (p<0.05), and content of LPO and MDA significantly increased (p<0.01). Compared with the model control group, the SOD activity of rats in the composition groups 1, 2, 3, 4 and 5 significantly increased (p<0.01), and the content of LPO and MDA significantly decreased (p<0.01). The content of LPO and MDA of rats in the composition groups 4 and 5 was lower than that of the composition group 1 (p<0.01 or p<0.05). The SOD activity of the control sample groups 1, 2 and 3 was significantly lower than that of the composition groups 1, 2, 3, 4 and 5 (p<0.01 or p<0.05), and the content of LPO and MDA was significantly higher than that of the composition groups 1, 2, 3, 4 and 5 (p<0.01). $E_{composition\ 1}$ Q value=$E_{composition\ 1}$/($E_{control\ sample\ 1}$+$E_{control\ sample\ 3}$−$E_{control\ sample\ 1}$×$E_{control\ sample\ 3}$)=0.470/(0.205+0.197−0.205×0.197)=1.061, 0.85<1.06<1.15, indicating that the combination of control sample 1 and control sample 3 has an additive effect, working together to increase the level of SOD. $E_{composition\ 1}$ Q value=$E_{composition\ 1}$/($E_{control\ sample\ 1}$+$E_{control\ sample\ 3}$−$E_{control\ sample\ 1}$×$E_{control\ sample\ 3}$)=0.463/(0.094+0.130−0.094×0.130)=2.179, 2.179>1.15, indicating that the combination of control sample 1 and control sample 3 has a synergistic effect on decreasing the LPO. $E_{composition\ 1}$ Q value=$E_{composition\ 1}$/($E_{control\ sample\ 1}$+$E_{control\ sample\ 3}$−$E_{control\ sample\ 1}$× $E_{control\ sample\ 3}$)=0.566/(0.220+0.233−0.220×0.233)=1.408, 1.408>1.15, indicating that the combination of control sample 1 and control sample 3 has a synergistic effect on decreasing the MDA.

3. Statistics of Clinical Application

The sample of composition 1 was used as the test sample.

3.1 Selected conditions: samples of subjects having slight mammary gland pain and moderate mammary gland pain were suitable samples, and samples that had developed into lesion were removed. The actual subjects were 122.

3.2 Reference was made according to the standard adopted by the 8th meeting of the Breast Diseases Professional Committee of the Traditional Chinese Surgery Branch of Chinese Medicine Association in 2002. Doctors assessed symptoms and signs using hand diagnose according to the degree of breast pain, degree of breast tenderness, size of lump, texture of lump and distribution range of lump.

Figure 2:
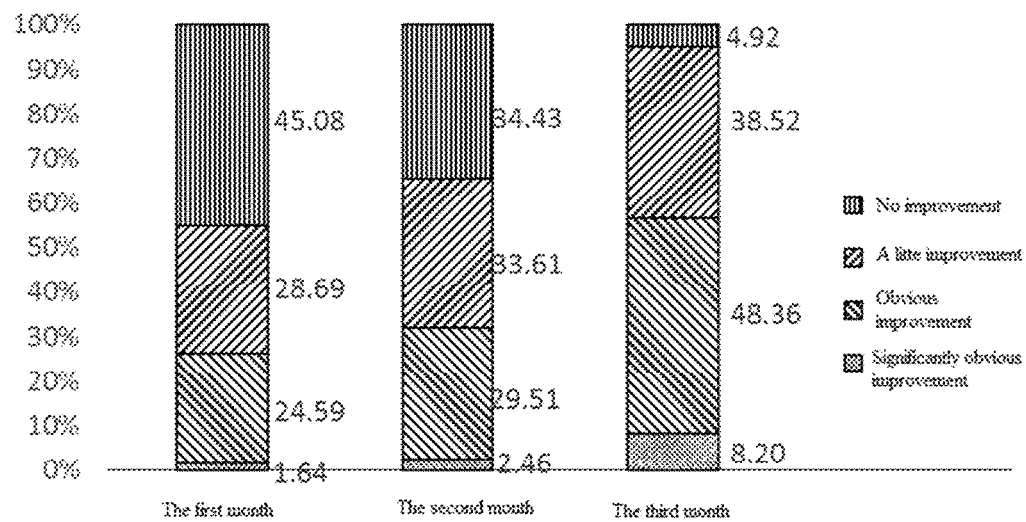
FIG. 2 shows a total evaluation of improvement of breast pain after administering with compositions (N=122,%), very obvious improvement=5-6 points; obvious improvement=3-4 points; a little obvious improvement=1-2 points; and no improvement=0 point.

3.3 Pain was evaluated with reference to the visual analogue scale (VAS). The method was widely used in clinical practice. The same method was used before and after clinical treatment to make a relatively objective score, and to make a relatively objective evaluation on the effect of pain treatment. VAS gives its breast pain scores according to the internationally recognized self-pain assessment based on the number representing the pain level on the "scale", in which 0-10 points indicates painless to severe pain. The results are shown in FIGS. 1-2.

3.4 According to the self-perceived pain score of the subjects, after administration of the products for three months, 56.56% of the subjects had a significant improvement in pain, 38.52% of the subjects had a slight improvement, and only 4.92% of the subjects had no improvement in the pain scores, fully indicating that the traditional Chinese medicine composition had a significant effect on improving breast pain.

Figure 3:
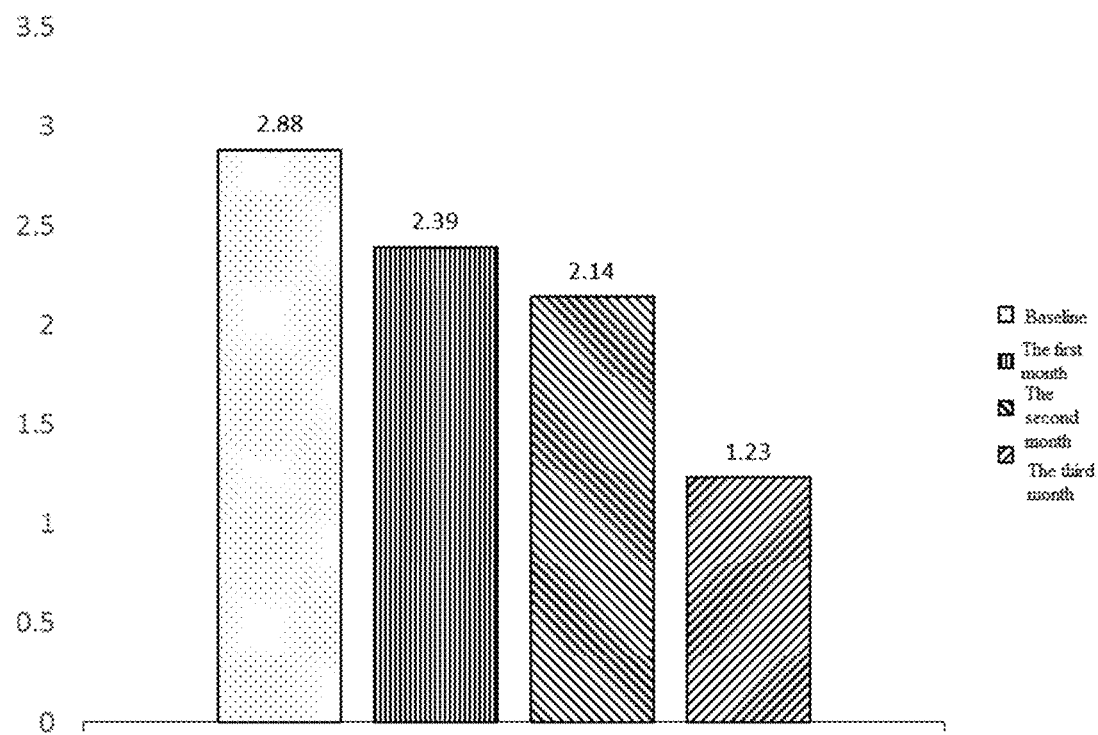
FIG. 3 shows average number of days of breast pain during the administration period of the composition (N=122, mean); "*" represents the baseline of the group, and compared with the first, the second, and the third month, the difference is significant (p<0.05).
Figure 4:
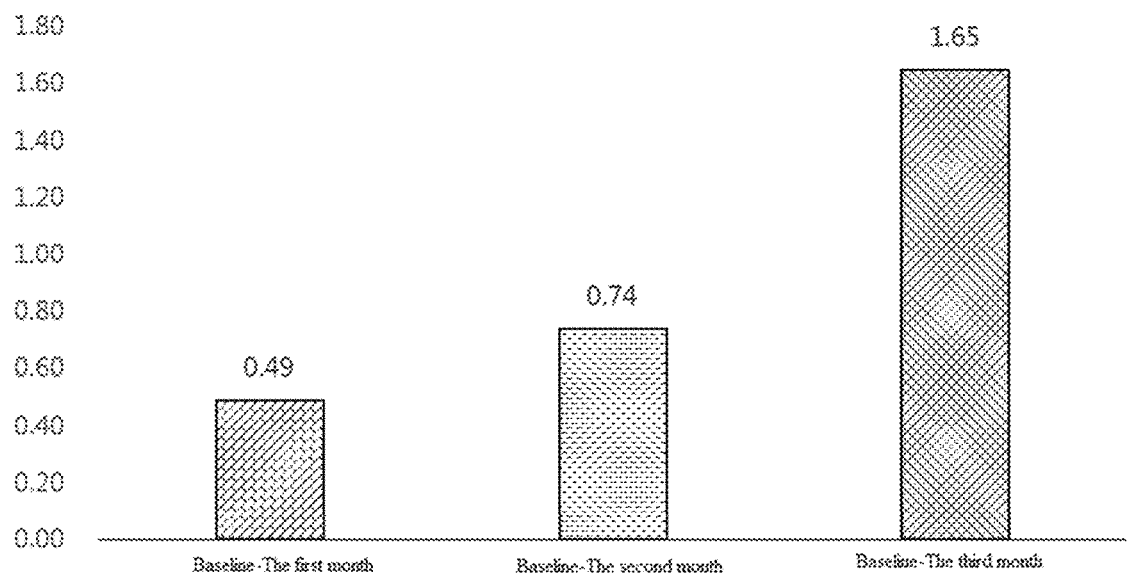
FIG. 4 shows the improvement of the number of days of breast pain before and after the administration of the composition (the value in the figure is the difference from that in 0 week).

3.5 According to FIGS. 3-4, after cured the products for one month, compared with the baseline period, the number of days of breast pain in the subjects administrated with the traditional Chinese medicine composition significantly reduced (p<0.05). As the administration time increased, the number of days of breast pain in the subject decreased. Three months after administration of the traditional Chinese medicine composition, the number of days of breast pain in the subjects decreased by 1.65 days.

3.6 Reference was made according to the standard adopted by the 8$^{th}$ meeting of the Breast Diseases Professional Committee of the Traditional Chinese Surgery Branch of Chinese Medicine Association in 2002. Improvement rates of before and after the treatment were calculated: improvement rate=(total score before treatment−total score after treatment)/total score before treatment×100%. Cured: improvement rate>90%, obviously effective: improvement rate 70%-89%; effective: improvement rate 30%-69%; and not effective: improvement rate<30%.

Total effective rate=cured rate+obviously effective rate+effective rate.

Figure 5:
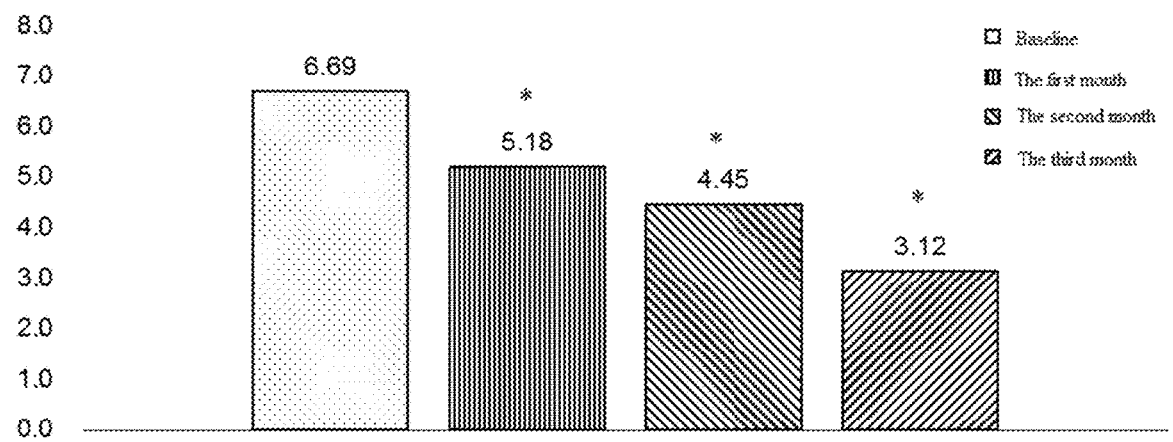
FIG. 5 shows the evaluated average value of symptoms and signs before and after the administration of the composition; "*" represents that compared with the initial values, the difference is significant (p<0.05).
Figure 6:
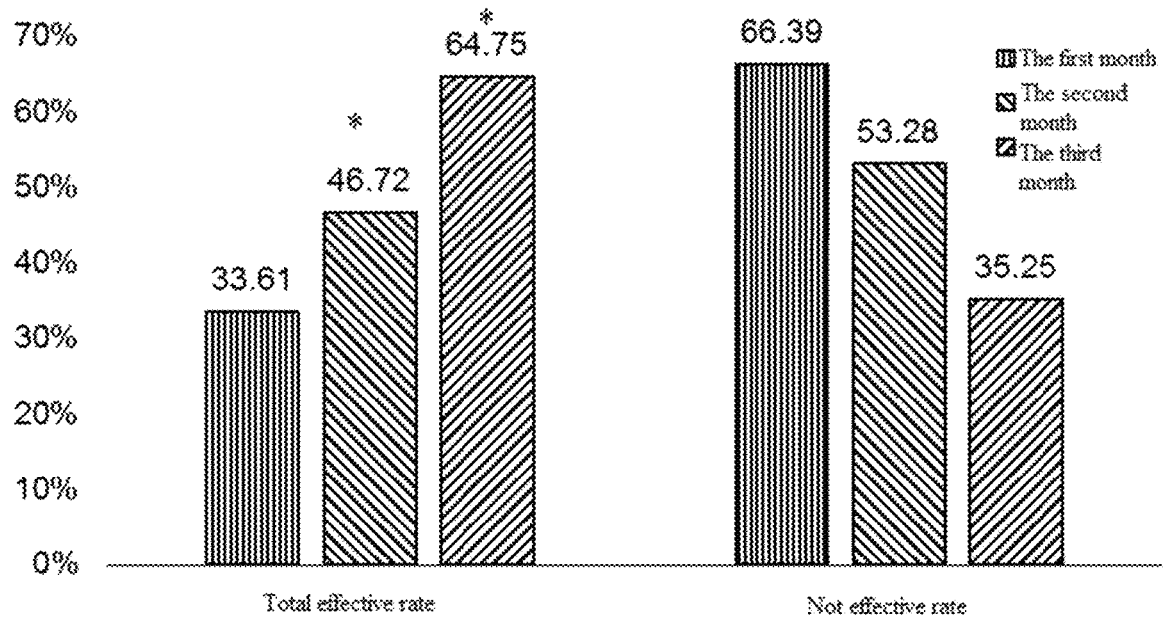
FIG. 6 shows the improvements of symptoms and signs (N=122, %).

FIGS. 5-6 showed the improvements in the subjects after administration of the traditional Chinese medicine composition. From the symptoms and signs obtained by hand diagnose of specialists, after administration of the composition for three months, the average value of breast symptom and signs of the subject decreased from 6.69 points to 3.12 points. From the aspect of improvement in total effective rate, the total effective rate reached 64.75% after three months with a statistical difference ($p<0.05$).

Comment: "*" represented that compared with the initial vale, the difference was significant ($p<0.05$).

Figure 7:
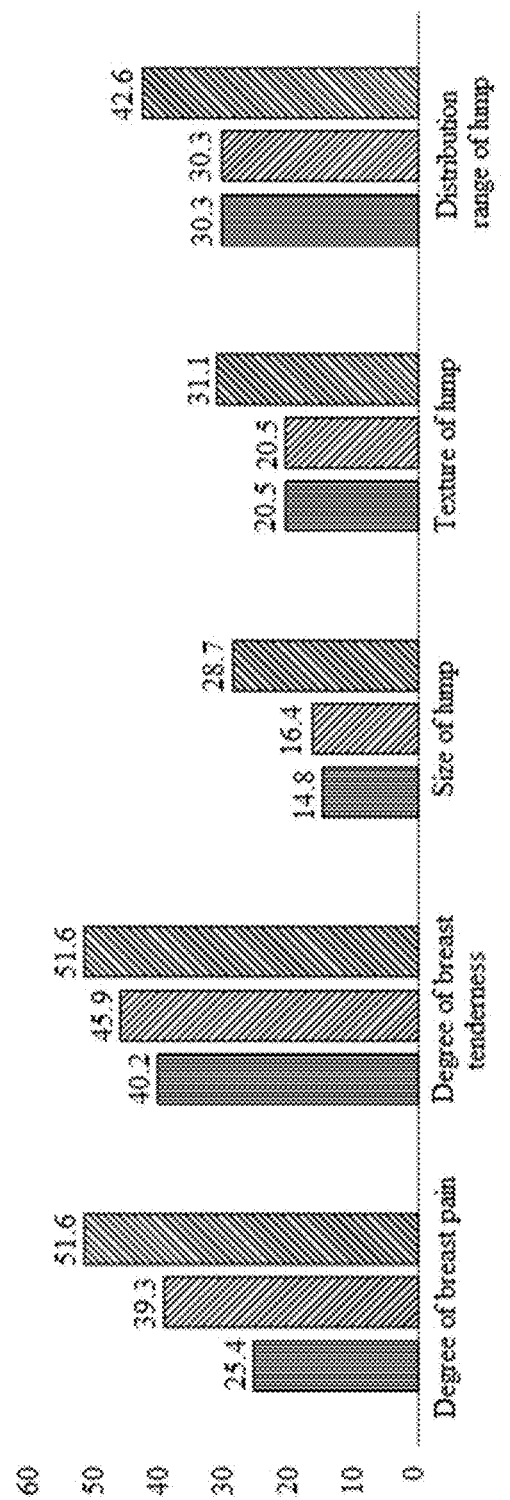
FIG. 7 shows the proportion of people whose symptoms and signs are improved (N=122, %).

3.7 As it shown in FIG. 7, after administration of the product for 1 month, degree of breast tenderness of the subject obviously improved (40.2%), and the other indicators improved in some degree. As the administration time increased, each symptom and sign in the subjects gradually improved. After administration of the traditional Chinese medicine composition for three months, degree of breast pain, degree of breast tenderness, size of the lump, texture of the lump and the distribution range of the lump in the subject obviously improved ($p<0.05$). Especially, degree of breast pain (51.5%) and degree of breast tenderness (51.6%) improved the most obviously.

The above are only preferred embodiments of the present disclosure. It should be noted that a number of modifications and refinements may be made by one ordinary skilled in the art without departing from the principles of the disclosure, and such modifications and refinements are also considered to be within the scope of protection of the disclosure.

What is claimed is:

1. A method for regulating endocrine hormone levels, regulating expression levels of estrogen receptor and/or progesterone receptor, improving hyperplasia of mammary gland, or resisting oxidation in a subject in need thereof, comprising administering to the subject a therapeutically effective amount of a composition, wherein the composition consists of the following components in parts by weight

| | |
|---|---|
| Rehmanniae Radix Praeparata | 10 parts-200 parts; |
| Lycii Fructus | 8 parts-100 parts; |
| Polygonati Rhizoma | 8 parts-100 parts; |
| Radix Codonopsis Pilosulae | 4 parts-50 parts; |
| Paeoniae Radix Alba | 4 parts-50 parts; |
| Cyperi Rhizoma processed with vinegar | 4 parts-50 parts; and |
| Vitis vinifera seed | 1 part-30 parts. |

2. The method according to claim 1, wherein endocrine hormone is estradiol, progesterone, luteinizing hormone, follicle stimulating hormone and/or prolactin.

3. The method according to claim 1, wherein improving hyperplasia of mammary gland comprises improving diffuse hyperplasia of mammary gland, improving breast pain and/or improving breast tenderness.

4. The method according to claim 1, wherein the resisting oxidation comprises lowering LPO and/or MDA levels in serum, improving total anti-oxidative capacity, improving GSH-PX enzyme activity, and improving SOD enzyme activity.

5. The method according to claim 1, wherein the composition consists of the following components in parts by weight

| | |
|---|---|
| Rehmanniae Radix Praeparata | 30 parts-150 parts; |
| Lycii Fructus | 40 parts-80 parts; |
| Polygonati Rhizoma | 40 parts-80 parts; |
| Radix Codonopsis Pilosulae | 10 parts-50 parts; |
| Paeoniae Radix Alba | 10 parts-50 parts; |
| Cyperi Rhizoma processed with vinegar | 10 parts-50 parts; and |
| Vitis vinifera seed | 1 part-20 parts. |

6. The method according to claim 1, wherein the composition consists of the following components in parts by weight

| | |
|---|---|
| Rehmanniae Radix Praeparata | 90 parts; |
| Lycii Fructus | 60 parts; |
| Polygonati Rhizoma | 60 parts; |
| Radix Codonopsis Pilosulae | 30 parts; |
| Paeoniae Radix Alba | 30 parts; |
| Cyperi Rhizoma (processed with vinegar) | 30 parts; and |
| Vitis vinifera seed | 7 parts. |

* * * * *